(12) United States Patent
Doelle et al.

(10) Patent No.: US 7,927,836 B2
(45) Date of Patent: Apr. 19, 2011

(54) DEVICE AND METHOD FOR THE PRODUCTION OF BIOLOGICALLY ACTIVE COMPOUNDS BY FERMENTATION

(75) Inventors: Bernd Doelle, Alzenau (DE); Michael Pfeil, Konigstein Im Taunus (DE)

(73) Assignee: Merz Pharma GmbH & Co. KGaA, Frankfurt am Main (DE)

(*) Notice: Subject to any disclaimer, the term of this patent is extended or adjusted under 35 U.S.C. 154(b) by 662 days.

(21) Appl. No.: 12/001,959

(22) Filed: Dec. 13, 2007

(65) Prior Publication Data
US 2008/0187967 A1    Aug. 7, 2008

Related U.S. Application Data

(63) Continuation of application No. PCT/EP2006/005272, filed on Jun. 2, 2006.

(30) Foreign Application Priority Data

Jun. 17, 2005 (DE) .......................... 10 2005 028 171

(51) Int. Cl.
  C12P 21/04 (2006.01)
  C12M 1/36 (2006.01)
  C12M 1/12 (2006.01)
  C12M 1/02 (2006.01)
  C12M 1/21 (2006.01)

(52) U.S. Cl. ................. 435/71.3; 435/286.5; 435/297.1; 435/297.4; 435/303.1; 435/303.2; 435/809

(58) Field of Classification Search .................. None
See application file for complete search history.

(56) References Cited

U.S. PATENT DOCUMENTS

| 3,775,256 A | 11/1973 | Risinger et al. |
| 4,262,091 A | 4/1981 | Cox et al. |
| 5,424,209 A * | 6/1995 | Kearney ...................... 435/286.5 |

FOREIGN PATENT DOCUMENTS

| EP | 1 471 138 | 10/2004 |
| EP | 471138 | 10/2004 |
| EP | 1 548 099 | 6/2005 |
| EP | 1548099 | 6/2005 |
| JP | 58/081776 | 5/1983 |
| JP | 58081776 | 5/1983 |
| JP | 081452 | 3/2005 |
| JP | 2005081452 | 3/2005 |
| WO | 98/20106 | 5/1998 |
| WO | WO 9820106 | 5/1998 |
| WO | 00/74703 | 12/2000 |
| WO | WO0074703 | 12/2000 |
| WO | 02/05332 | 1/2002 |
| WO | WO0205332 | 1/2002 |
| WO | 2005/040330 | 5/2005 |
| WO | WO 2005040330 | 5/2005 |
| WO | 2006/027207 | 3/2006 |
| WO | WO 2006027207 | 3/2006 |

OTHER PUBLICATIONS

International search report for PCT/EP2006/005272 of Sep. 21, 2006.
Dasgupta, B.R. et al. in Toxicon, vol. 22, Nr. 3, 415-424, 1984.
International Search Report for PCT/EP2006/005272; Sep. 21, 2006.
IPRP for PCT/EP2006/005272; Dec. 17, 2007.
International preliminary report on patentability for PCT/EP2006/005272 of Jan. 24, 2008.

* cited by examiner

Primary Examiner — Herbert J. Lilling
(74) Attorney, Agent, or Firm — Hueschen and Sage

(57) ABSTRACT

The present invention relates to a process and an apparatus for the fermentational production of biologically active materials, wherein a fermenter is located in an insulator which, in turn, is located within a working chamber or is adjacent to it. A pressure gradient in relation to ambient pressure prevails in both the insulator and in the working chamber.

28 Claims, No Drawings

DEVICE AND METHOD FOR THE PRODUCTION OF BIOLOGICALLY ACTIVE COMPOUNDS BY FERMENTATION

FIELD OF THE INVENTION

The invention relates to a process and an apparatus for the fermentational production of biologically active materials wherein the fermenter is located in an insulator which in turn is located in a working chamber or is adjacent to it, and wherein a pressure gradient in relation to ambient pressure prevails in both the insulator and in the working chamber.

BACKGROUND OF THE INVENTION

Working with biologically active compounds requires increased safety measurements in the production facility to protect employees against potential hazards or intoxication. Biologically active compounds are often produced or used for pharmaceutical purposes which are the reasons why requirements of stringent cleanliness must be complied during manufacture. The routine construction of facilities for the manufacture of ultrapure compounds is composed of a first, internal chamber which is outwards closed and which is surrounded by a second chamber. In the second chamber the persons working with the biological material are residing, while the processing of the biological material occurs mainly in the first chamber. Both chambers are connected with each other through lockable sluices. The first chamber is typically a glovebox so that the process steps may be accomplished from the second chamber with the aid of gloves. The second chamber is typically insulated from the outside, but connected to it through lockable sluices. In both chambers there are ideally sterile conditions which satisfies clean room requirements. To prevent contamination of the biologically active material with surrounding particles, microbiological germs and the like, an over pressure prevails in the first chamber, which is typically an over pressure of 15 Pa. In contrast thereto, within the second chamber there exists a low pressure compared to the first chamber, but an over pressure in relation to the ambient pressure. Therefore, particles or germs from the second chamber will be prevented from infiltrating the first chamber. Thus, the biologically active material will be protected against contamination from the environment.

In the case of manufacture of biologically active compounds by a fermentational process, there are process steps which are carried out, at least temporarily, in an open apparatus. Inoculation is for example such a process step. In the majority of cases this step has to be conducted manually. During this procedure in which the device (container, vial) containing the starting material (cell bank) is opened, if only shortly, aerosols may be formed. Furthermore, during the intermediate steps of the preculture stages until the start of fermentation, a port of the fermenter may be opened, if only shortly, which may create aerosols. Likewise it is possible that during processing of the fermentation product, ie. the biologically active substance, aerosols may be formed. Thus there is a risk of exposing the environment to germs, bacteria or toxic substances. Because of the relative low pressure in the second chamber in relation to the first chamber, aerosols from the first chamber may infiltrate the second chamber and can lead to a threat for the persons working in the second chamber. Nevertheless, ensure operational safety, more precautions in this case must be set, as for example vaccination of the employees, wearing of protective clothing, etc.

OBJECT OF THE INVENTION

Thus, an object of the invention is to provide a process and an apparatus for production of biologically active materials by fermentation, wherein the materials will be protected against contamination from the environment and at the same time the exposure of the personnel to aerosols from the fermentation steps and processing of biological material will be reduced or completely prevented. The present invention solves this object by providing the apparatus and the process as described herein.

SUMMARY OF THE INVENTION

The invention inter alia comprises the following, alone or in combination:

An apparatus for the fermentative production of a biologically active compound, comprising at least a first insulator containing a fermenter, the first insulator being surrounded or adjacent to a working chamber, wherein the working chamber is connected to the environment via a pressure sluice, wherein a low pressure prevails in the insulator and in the working chamber, wherein the pressure (in relation to ambient pressure) in the insulator is lower than the pressure (in relation to ambient pressure) in the working chamber, and wherein an over pressure prevails in the pressure sluice in relation to ambient pressure, such an apparatus wherein the pressure in the insulator is 20 to 200 Pa lower than ambient pressure, such an apparatus wherein the pressure in the working chamber of 5 to 50 Pa is lower than ambient pressure, such an apparatus wherein the pressure in the pressure sluice of 10 to 100 Pa is higher than ambient pressure, such an apparatus wherein the apparatus comprises at least a second insulator, and wherein the second insulator does not contain a fermenter, such an apparatus wherein the apparatus and/or the first insulator and/or the second insulator comprise at least a supply air duct and an exhaust air duct, wherein the supply air duct and the exhaust air duct comprise a filter, selected from a HEPA filter, such an apparatus wherein the internal pressure of the first insulator is equal to the internal pressure of the second insulator, such an apparatus wherein the internal pressure of the first insulator is different than the internal pressure of the second insulator, such an apparatus wherein the first and the second insulator are connected with each other via a passage, wherein the passage allows for material transport from the first insulator to the second insulator and also allows for material transport from the second insulator to the first insulator, such an apparatus wherein the passage is a sluice, such an apparatus wherein the apparatus comprises a sterilizing facility and/or a disinfection facility, such an apparatus wherein the first insulator comprises an anaerobic working fermenter, such an apparatus wherein the first insulator comprises a precipitation facility, such an apparatus wherein the first insulator comprises a filtration facility, such an apparatus wherein the second insulator comprises an extraction facility, such an apparatus wherein the second insulator comprises a precipitation facility, such an apparatus wherein the second insulator comprises at least a chromatography facility, such a process for the fermentational production of a biologically active compound comprising a fermentation step for the production of the biologically active compound a purification step for the biologically active compound, wherein the process is conducted in the apparatus, such a process wherein the biologically active compound is a toxin or another protein obtained from fermentation, selected from a *botulinum* toxin and a *botulinum* neurotoxin, such a process wherein the *botulinum* toxin is a *botulinum* toxin belonging to *Clostridium botulinum* of types A, B, C, D, E, F, and G, or is a mixture of two or more of these types, such a process wherein the *botulinum* toxin or the mixture of *botulinum* toxins is/are a *botulinum* neurotoxin or a composition of *botulinum* neurotoxins, such a process wherein the fermentation step occurs in the first insulator and the purification (step) occurs totally or partially in a second insulator, such a process wherein the fermentation step and a part of the purification step occur in the first insulator and another part of the purification step occurs in the second insulator, such a process wherein the fermentation step, a precipitation and filtration of a product of the fermentation step, occur in the first insulator as a part of the purification step, such a process wherein the first insulator and the second insulator are operated at the same temperature or at different temperatures, such a process wherein the temperature in the first and/or the second insulator are changed according to each process step, such a process wherein the temperature in the first insulator is in a range of approximately 20° to approximately 50° C. and the temperature in the second insulator is in a range of approximately −5° to approximately +25° C., such a process wherein the process comprises the following steps:
i. in the first insulator
  inoculating fermentation media with a producing strain which produces a biologically active compound;
  fermenting the producing strain;
  separating supernatant from cells of the producing strain; and
  precipitating the supernatant;
ii. in the second insulator
  centrifuging the precipitated supernatant to obtain a pellet;
  extracting the pellet, centrifuging to obtain a supernatant;
  precipitating the supernatant with subsequent centrifuging to obtain a supernatant;
iii. in the first or the second insulator
  precipitating the supernatant;
  centrifuging the precipitate;
  solubilizing the pellet obtained by centrifuging the precipitate;
  dialysing the solubilized pellet and centrifuging the dialysate;
  performing chromatography of the dialysate;
  filtration of the dialysate to obtain an eluate.

DETAILED DESCRIPTION OF THE INVENTION

The present invention relates to an apparatus and a process for the production of biologically active agents via fermentation, in an ultrapure form, wherein contamination of the biological material with particles and germs from the environment will be prevented and, at the same time, the potential hazard to the personnel working with the biological material will be reduced. The fermentational process includes at least a step of inoculation. The fermentational process includes at least one step which is manually conducted, and may be the step of inoculation.

The process and the apparatus of the present invention allow for the use of approved production techniques and purification techniques which involve, or which could involve, aerosol formation. The process and the apparatus of the present invention reduces the potential for persons who are in charge of the production processes and/or the processing processes to be exposed to aerosol formation. In other words, the apparatus of the present invention and the process of the present invention reduce the risk of exposure of the environment to aerosols and reduces the risk of exposure for production personnel to the biologically active material, bacteria and/or germs. At the same time, the process and the apparatus of the present invention allows for the application of established techniques for efficient production and purification of a biological material, which may produce an aerosol.

The apparatus of the present invention includes at least an insulating chamber (insulator) being surrounded by a working chamber or being adjacent thereto. The working chamber is connected with the environment via a pressure sluice. Both in the insulator, as well as in the working chamber, a low pressure prevails compared to the pressure of the environment, wherein the pressure in the insulator is lower than the pressure in the working chamber. In the pressure sluice there prevails an over pressure in relation to the ambient pressure. The insulator contains at least a fermenter, in which the biologically active material will be produced by fermentation.

Using the apparatus of the present invention the biologically active material will be produced and/or processed in the insulator. An insulator, as used herein, is an airtight defined system as compared to the environment that stays in an energetic exchange with its environment, but does not allow for an uncontrolled transport of material with its environment. Controlled transport of material with its environment, for example the respective load or withdrawal of equipment, reagents, starting material, intermediate products, and end products, can be provided by one or more sluices, double trap container, i. e. so called β-ports in connection with α-containers or α-bags. Controlled transport of material is possible before, during or after the fermentation and/or the purification of the fermentation product or the biologically active material.

The insulator can be operated at over pressure or low pressure regulated through appropriate facilities. It is likewise possible that an atmosphere of inert gas will be generated in the insulator. The insulator typically operates on one or more supply air duct(s) and exhaust air duct(s) which are typically equipped with filters. Thus in the insulator, the number of germs may be less than 100 germs/m$^3$, less than 10 germs/m$^3$, and less than 1 germ/m$^3$. Such filters are known to one of skill in the art. An example for such filter is a HEPA (high efficiency particulate filter) filter.

The equipment, apparatuses, or objects situated in the insulator can be moved or operated via a control system from the outside or via glove inlets attached to the insulator which may be actuated from the working chamber.

The insulator is preferably made completely or partially from a material which is biologically inert and easy to clean and which allows for an in situ decontamination or sterilization, respectively. Therefore a material is preferred which allows for sterilization with formalin, ethylene oxide or vaporous hydrogen peroxide (VHP). Such materials include, for example, glass, stainless steel or polymers, such as PVC. Preferably the insulator is manufactured so that the interior surface thereof is completely or partially made of glass, stainless steel or other appropriate materials, such as polymers. Thus both hard and also soft polymers (hard and soft wall insulators) can be used. Gloves are typically made from neoprene, hypalone, vinyl or other suitable materials.

Typically the insulator disposes of an installation for temperature control and temperature regulation.

Typically the insulator is situated in, or abuts to, a working chamber. There is a pressure gradient between the insulator and the working chamber. Thereby, a lower pressure prevails in the insulator compared to the one in the working chamber which, in turn, exhibits a lower pressure compared to ambient pressure. The ambient pressure accounts for 101,325 Pa, but may be varying depending on geographical position or meteorological conditions.

Typically the operating pressure in the insulator is a low pressure in the range of 20 to 200 Pa, in the range of 40 to 100 Pa, and in the range of 55 to 75 Pa, respectively compared to ambient pressure (101,325 Pa).

Usually the operating pressure in the insulator is approximately 10 to 100 Pa, approximately 20 to 80 Pa, approximately around 40 to 60 Pa lower compared to the working chamber.

In an embodiment of the invention, the typical value of the pressure difference between the insulator and the working chamber, within metrological and equipment dependant fluctuations, lies in the range of 35 to 57 Pa and around 45 Pa, i.e. the pressure in the insulator respectively is approximately 35 to 57 Pa or approximately 45 Pa lower than the one in the working chamber.

The supply of air into and out of the insulator preferably passes through filters, such that a maximum number of 100 germs/$m^3$, a maximum of 10 germs/$m^3$ or a maximum of 1 germ/$m^3$ may be in the insulator.

The working chamber of the present invention is an airtight sealed system which is connected with an airtight seal with the insulator for the purpose of an exchange of matter or equipment through one or more lockable openings. Furthermore, it is connected through at least one lockable pressure sluice for the exchange of matter or equipment and/or acquisition in an airtight manner. The working chamber surrounds or abuts to the insulator. The supply of air into and out of the working chamber preferably passes through filters, such that a maximum number of germs may be 200 germs/$m^3$, a maximum number of 100 germs/$m^3$, or a maximum number of 10 germs/$m^3$ may be in the working chamber. Such filters are for example available in trade under the name HEPA filters.

The working chamber may exhibit a temperature of around 19° C. to 26° C. and a relative humidity of 40 to 60%. The first and the second insulator, independent from each other, may exhibit a temperature and a relative humidity which is common and suitable for the performance of the production and the purification of the biologically active material.

In the working chamber an operating pressure prevails which is higher than the one in the insulator, but there exists a pressure gradient in relation to the ambient pressure and to the pressure sluice.

Typically the pressure in the working chamber is 5 to 50 Pa, 10 to 30 Pa, or 12 to 18 Pa lower than compared to ambient pressure.

In an embodiment of the invention, a typical value of the pressure difference, within metrological and equipment dependent fluctuations, is 15 Pa compared to ambient pressure, i.e. the pressure in the working chamber is approximately 15 Pa lower than the ambient pressure.

The working chamber is connected to the environment via at least one lockable pressure sluice. In the sluice there is an over pressure in relation to ambient pressure of 10 to 100 Pa, preferably 20 to 80 Pa, and most preferably 25 to 35 Pa.

Generally a pressure difference exists between the pressure sluice and the working chamber of 10 to 200 Pa, preferably 20 to 100 Pa, and most preferably 40 to 60 Pa.

In an embodiment of the invention, a typical value of the pressure difference between the pressure sluice and the working chamber, within metrological and equipment dependant fluctuations, is 45 Pa, i.e. the pressure in the working chamber is approximately 45 Pa lower than the ambient pressure.

Generally a pressure difference exists between the pressure sluice and the insulator of 10 to 300 Pa, preferably 50 to 200 Pa, and most preferably 80 to 100 Pa. A typical value of the pressure difference between the pressure sluice and the insulator, within metrological and equipment dependant fluctuations, is 90 Pa, i.e. the working pressure in the insulator is approximately 90 Pa lower than in the pressure sluice.

In another embodiment, the apparatus of the present invention comprises at least one other insulator. This at least one other insulator can be situated in the same working chamber as the first insulator, or can abut to the same working chamber, it also can be connected airtightly to the first insulator, for example through one or more lockable sluices, double trap container or ports. The insulators, however, need not be connected with each other. The at least one other insulator may have the same features as the first insulator which is described above.

In the insulator of the present invention a fermentation step will typically be performed. The fermentation step may be one in which a biologically active material will be produced. This fermentation step may include one or more inoculations. Thus the insulator of the present invention contains at least one fermenter.

Typically in the insulator, one or more steps or measures which are necessary for the purification of the biological material may also be executed. Therefore fermentation and purification may be executed in one and the same insulator or in different insulators, for example, the fermentation carried out in the first insulator and the purification carried out in the second insulator.

The fermentation step, which may involve the synthesis of a biologically active material, occurs in a fermenter. Depending on the producing strain which produces the biologically active material, one may selective an anaerobic or an aerobic working fermenter. The fermenter is constructed and equipped in accordance with the particular fermentation conditions, in accordance with the knowledge of those skilled in the art. The fermenter can be a fermenter for the batch fermentation, the semi-batch fermentation or the continuous fermentation.

The fermentation step may also comprise the precultivation or the initial cultivation to inoculate the main fermenter. The different measures and the corresponding procedural equipment which are required for this purpose are known for those skilled in the art and comprise among other things one or more fermenters which allow a first and/or a second expansion of the stock of the producing strain which produces the biologically active material. The measures associated therewith also comprise, for example, the establishment of a working cell bank, the first expansion of cell material, the second expansion of cell material and the actual fermentation step. The actual fermentation step concerns the growth of cells for the synthesis of the biologically active compound. These steps may be executed at the optimal temperature or temperature gradient respective of the producing organism. Therefore the temperature will be, if applicable, continuously or discontinuously adapted to the production conditions.

It is possible that one or more steps or measurements which are necessary for the purification of the biologically active material will be executed in the insulator. Accordingly the insulator contains the equipment necessary for it.

The purification of the biologically active material may also be conducted in a second insulator of the apparatus of the present invention. As only a part of the measures for purification are conducted in the second insulator, the remaining part of the necessary measurements will be conducted in the first insulator or in one or more further insulators.

Certain measurements which are involved in the production of biologically active material may also be executed outside of an insulator, particularly those steps not associated with aerosol formation or in instances where the biologically active material is available in a form, or in a container, from which one assumes no hazards for the environment or for the persons engaged with the production or operation.

The fermentation which generates the biologically active material may include fermentation of bacteria, including bacteria of the *Clostridium botulinum* family. This is also applicable for recombinant or genetically modified *Clostridium botulinum* strains as well as for other recombinant or genetically modified heterologous expression systems (e. g. *E. coli*).

Using the installed equipment, all biologically active compounds, for example, proteins, which will be synthesized by fermentational growing of microorganisms, may in principle be produced.

The biologically active compound which may be produced by using the fermentation process may be a toxin, including a *botulinum* toxin and a *botulinum* neurotoxin.

*Botulinum* toxin is produced by the bacterium *Clostridium botulinum* and exists in different serotypes: *botulinum* toxin type A, B, C, D, E, F, G. The botulinum toxin produced by *Clostridium botulinum* is a complex of the *botulinum* neurotoxin, i. e. the protein which is responsible for the toxic effect, and complexing proteins which, as such, are non toxic. These complexing proteins are hemagglutinins with different molar masses, as well as at least one non hemagglutinating protein. The complexes from *botulinum* neurotoxin and the (bacterial) complex proteins are in general termed *botulinum* toxin. The complexes of the types A, B, and C are commercially available, type A for example as BOTOX®. These complexes may be further processed in order to yield complexes of different protein composition and purity, including a botulinum neurotoxin without complexing proteins. Therefore within the scope of this invention the term *botulinum* neurotoxin will be used to describe the protein which is responsible for the toxic effect, i.e. the *botulinum* toxin that is free of bacterial complexing proteins. The *botulinum* toxin type A has a molecular mass of approximately 150 kDa and is commercially marketed under the trade name Xeomin® by the applicant.

Eligible within the scope of this invention are all forms of the "*botulinum* toxin", especially the different serotypes, the different complexes of *botulinum* neurotoxin and complex proteins, the *botulinum* neurotoxin itself, as well as modified or corresponding recombinantly produced *botulinum* toxins, or *botulinum* neurotoxins including mutations, deletions etc. Such mutant forms may be those which are described in WO 2006/027207 A1. Furthermore, within the scope of the invention is the production of mixtures of different serotypes (in a complexed and/or uncomplexed and/or recombinant form), e. g. mixtures of *botulinum* toxins of the types A and B or mixtures of neurotoxins of the types A and B.

The production of *botulinum* neurotoxin of the types A and B is described, for example, in the International Patent Publication No. WO 00/74703. The characteristics of the (isolated) *botulinum* neurotoxin, including being substantially non-immunogenic, are advantageous over a *botulinum* neurotoxin with complexing proteins, hence there is a tremendous need to provide apparatuses and processes for the safe and reliable industrial production of *botulinum* neurotoxin, which is provided by the present invention.

The selection and/or the number of insulators may be selected by those skilled in the art depending on the biological compound to be produced. With the purification described herein in more detail, the use of at least two insulators are advantageously used. Thus the insulators may vary with respect to the temperature which predominates therein or in a portion therein. Thus, within the scope of the present invention, the first insulator will be operated at a higher temperature, e. g. at around 200 to 50° C., and the second insulator will be operated at a lower temperature, for example in the range of about −50 to +25° C. Thus, those steps which necessitate an adequate higher temperature, or which can be executed at this temperature, including the steps of production, as well as those of purification, are conducted in the first insulator. That includes especially the inoculation, the fermentation and/or the precipitation of the producing strain. On the contrary, those steps of the production process which necessitate an adequate lower temperature, especially for the purification of the neurotoxin, are executed in a second insulator and are conducted in a beneficial manner at this lower temperature range.

It will be further appreciated that those steps of the production in general, and of the fermentation and purification in particular, which can be conducted in both temperature ranges, and therefore in each of the two insulators, may be finally conducted in the one insulator which is advantageous in view of its dimensioning, and of the energy consumption as a result of the dimensioning, for the maintenance of the appropriate reaction conditions and for the performance of the reaction steps, especially the temperature, or in view of manageability or feasibility of the individual measures.

The second insulator is in principle similarly built as the first insulator, but is provided with facilities and equipment or technical equipment features according to the apparatus. The second insulator may be required for the conduction of the purification steps or for the measures thereof. Purification steps which may be conducted in the second insulator are selected from precipitation, extraction, centrifugation, dialysis and chromatography. Accordingly, the second insulator may include one or more precipitation facilities, extraction facilities, centrifugation facilities, dialysis facilities and/or chromatography facilities. A precipitation facility comprises a reaction container in which the solution for performing the precipitation is contained, equipped with a feeding pipe to add the compound(s) required for precipitation. In addition, the precipitation facility basically comprises measures for taking out the supernatant as well as the precipitate. Appropriate facilities are known to those skilled in the art. An extraction facility typically comprises a reaction container in which the solution for extraction is contained, a feeding pipe for adding the extraction medium as well as a device to separate the fluid which contains the extract from the extracting fluid. A centrifugation facility typically comprises a centrifuge to separate solid-solid mixtures or liquid-solid mixtures. The chromatography facility typically comprises a chromatography column which is filled with a chromatography material as well as an inlet and an outlet and containers with appropriate media both to feed the chromatography column and to elute. The used chromatography is, e.g., size exclusion chromatography, HPLC or affinity chromatography.

Within the scope of the present invention is the inclusion of two or more insulators which are connected with each other in such a way that the entirety of the apparatus, which comprises both insulators, contains a supply air duct and an exhaust air duct, and that both insulators are connected with one or more intermediate ducts. Therefore, it is also within the scope of the present invention that the first insulator, as well as the second insulator and/or any further insulator, comprise in each case and independent from each other, a supply air duct and an exhaust air duct.

The first and the second insulator preferably exhibit an internal pressure which is lower compared to the external pressure. At the same time it is within the scope of the present invention that both insulators exhibit an identical internal pressure. It is, however, also within the scope of the present invention that both insulators exhibit different internal pressures. Therefore, the internal pressure of the insulator may be lowered in instances in which the likelihood of aerosol formation is higher due to the process steps which are performed in the respective insulator.

If using two insulators, the availability of a connection between the insulators in the form of a passage, for example in form of a sluice, between both insulators is advantageous. The presence of a sluice ensures that the transfer of both the produced and purified material to the different steps of the production and processing can occur without breaking through the barrier built by the insulator. The design of the apparatus and of each of the insulator or at least of one insulator of the apparatus of the present invention with a sterilization device serves the same objective. Similar sterilization devices are known to those skilled in the art and comprise for example a generator for the generation of vaporous hydrogen peroxide. Therefore, the use of vaporous hydrogen peroxide is especially beneficial in view of the under pressure conditions.

In a further aspect, the present invention relates to a process for the fermentational production of a biologically active compound wherein the process comprises a fermentation step for the production of the biologically active compound and a purification step of the biologically active compound, in which the fermentational production and/or the purification will be completely or partially executed in one or more insulators. The fermentation step and one or more parts of the purification of the biological material occur in a first insulator, and one or more parts of the purification may occur in a second insulator. The fermentation step includes at least an inoculation step which is manually conducted. It is also within the scope of the present invention that further insulators will be used. The biologically active material may concern a botulinum toxin, especially a *botulinum* neurotoxin, as described herein. The features which are disclosed in connection with the present invention also exhibit features, either alone or in any combination of the process of the present invention.

Measures in connection with the work-up are centrifugation, dialysis, extraction, precipitation, protamine sulfate precipitation, ammonium sulfate precipitation, solubilizing of precipitates which generally occur as pellets, dialysis, chromatography steps or chromatography processes and filtration. Concerning the chromatography process it is a succession of several individual chromatography processes. Thus, in each case it can be the same chromatography process or of different chromatography processes. If a pharmaceutical active compound is *botulinum* neurotoxin type A, it is a matter of succession of three chromatography steps using proper column material. Therefore, it is possible and preferred that the particular eluate will undergo a dialysis before application onto the next column.

The *Clostridium* strain which may be used in a fermentation is *C. botulinum* type A which has been stored in a suitable medium at temperatures which guarantee stability. For fermentation, the process described by DasGupta B. R. et al. in Toxicon, vol. 22, No. 3, p. 414 to 424, 1984, may be used. Therefore, 0.5% yeast extract and 0.6% autoclaved yeast paste is added to 2% of the N-Z-amine type A medium, and adjusted to a pH of 7.2 by the addition of 4N NaOH and is autoclaved. To this medium, separately autoclaved glucose (20% by weight per volume) is added, for a final concentration of glucose of 0.5% in the medium. Incubation of the producing strain is done at 37° C. without stirring, and the fermentation was discontinued after 96 hours. It is within the scope of the present invention that besides the batch fermentation described before also semi-batch fermentation, repeated batch fermentation or continuous fermentation can be performed. The measurements required for this purpose and the requirements concerning the apparatus are known to those skilled in the art.

After the actual fermentation and separation of the fermentation medium from the cells, the fermentation medium will undergo a first precipitation with the goal to remove large proteins. This precipitation may be performed in the first insulator. The centrifugation of the precipitate obtained may be conducted in the second insulator. The precipitation may be an acid precipitation. Reaction conditions for such an acid precipitation are known to those skilled in the art. Typically 3 N $H_2SO_4$ is used to acidify the supernatant to pH 3.5. The centrifugation usually occurs for 20 minutes at 2400×g at 4° C. The pellet obtained through centrifugation is washed with water, and the wash is repeated to obtain a pellet.

In a further step starting from the pellet, the precipitate will again be dissolved with the objective to release the toxin from the pellet. Measures for that are known to those skilled in the art and are described, among others, by DasGupta B. R. et al. (aaO). For example the extraction via a 0.1M citric acid-trisodium citrate buffer, pH 5.5 can be performed for an hour. Thereafter this extraction is followed by a further centrifugation step, usually at 9800×g for 20 minutes at 4° C. The so obtained pellet optionally can then again be extracted as described before. The supernatant of the extraction, and both supernatants in case of repetition of the extraction, were then subjected to protamine sulfate precipitation. The precipitation continued at 8° C. overnight. Afterwards the precipitate was again centrifuged for 20 minutes at 4° C. and at 12,000×g. At the protamine sulfate precipitation step especially DNA was removed.

The supernatant obtained after centrifugation is subject to an ammonium sulfate precipitation either in the first insulator or in the second insulator, whereby other larger proteins will be removed. After the ammonium sulfate precipitation step, another centrifugation step is conducted and subsequently the obtained pellet is re-dissolved and is optionally subjected to a dialysis. The extract which has been dialysed, and which is obtained from the pellet, is centrifuged again and may be subjected to a succession of chromatography steps with the objective to purify the *botulinum* neurotoxin, especially to purify to homogeneity. Each of the chromatography steps serves thereby to remove the protamine sulfate, remaining DNA, parts of smaller proteins and middle-sized proteins as well as the hemagglutinins of the *botulinum* neurotoxin protein complex. For this purpose a succession of several chromatography steps will be executed in an embodiment of the present invention. The eluate may then be filtrated. The filtration serves to reduce germs of the eluate, the eluate contains the pure *botulinum* neurotoxin without complexing proteins. Optionally, the eluate may be diluted before filtration and accordingly suitable adjuvants may be added.

During further steps, another sterile filtration may be conducted after addition of the adjuvants. Therefore, the filtration takes place in reaction containers which then will be subject to a lyophilization in a separate process step. The product lyophilized in such a way is sealed.

It will be appreciated by those skilled in the art that previous to inoculation, as well as after different process steps, especially the ammonium sulfate precipitation and the filtration in the first container, the container comprising product will be subject to decontamination and accordingly to sterilization. The sterilization may be performed via vaporous hydrogen peroxide (VHP).

The features of the invention disclosed in the preceding description and in the claims may be essential for the implementation of the invention in their different embodiments either alone or in any combination.

The invention claimed is:

1. An apparatus for the fermentative production of a biologically active compound, comprising at least a first insulator containing a fermenter, the first insulator being surrounded by a working chamber, wherein the working chamber is connected to the environment via a pressure sluice, wherein a low pressure prevails in the insulator and in the working chamber, wherein the pressure (in relation to ambient pressure) in the insulator is lower than the pressure (in relation to ambient pressure) in the working chamber, and wherein an over pressure prevails in the pressure sluice in relation to ambient pressure.

2. The apparatus according to claim 1, wherein the pressure in the insulator is 20 to 200 Pa lower than ambient pressure.

3. The apparatus according to claim 1, wherein the pressure in the working chamber of 5 is 50 Pa lower than ambient pressure.

4. The apparatus according to claim 1, wherein the pressure in the pressure sluice of 10 to 100 Pa is higher than ambient pressure.

5. The apparatus according to claim 1, wherein the apparatus comprises at least a second insulator, and wherein the second insulator does not contain a fermenter.

6. The apparatus according to claim 1, wherein the apparatus and/or the first insulator and/or the second insulator comprise at least a supply air duct and an exhaust air duct, wherein the supply air duct and the exhaust air duct comprises a filter, selected from a HEPA filter.

7. The apparatus according to claim 5, wherein the internal pressure of the first insulator is equal to the internal pressure of the second insulator.

8. The apparatus according to claim 5, characterized in that the internal pressure of the first insulator is different to the internal pressure of the second insulator.

9. The apparatus according to claim 5, wherein the first and the second insulator are connected with each other via a passage, wherein the passage allows for a material transport from the first insulator to the second insulator and also allows for a material transport from the second insulator to the first insulator.

10. The apparatus according to claim 9, wherein the passage is a sluice.

11. The apparatus according claim 1, wherein the apparatus comprises a sterilizing facility and/or a disinfection facility.

12. The apparatus according to claim 1, wherein the first insulator comprises an anaerobic working fermenter.

13. The apparatus according to claim 1, wherein the first insulator comprises a precipitation facility.

14. The apparatus according to claim 1, wherein the first insulator comprises a filtration facility.

15. The apparatus according to claim 5, wherein the second insulator comprises an extraction facility.

16. The apparatus according to claims 5, wherein the second insulator comprises a precipitation facility.

17. The apparatus according to claim 5, wherein the second insulator comprises at least a chromatography facility.

18. A process for the fermentational production of a biologically active compound comprising:
a fermentation step for the production of the biologically active compound,
a purification step for the biologically active compound,
wherein the process is conducted in the apparatus according to claim 1.

19. The process according to claim 18, wherein the biologically active compound is a toxin or another protein obtained from fermentation, selected from a *botulinum* toxin and a *botulinum* neurotoxin.

20. The process according to claim 19, wherein the *botulinum* toxin is a *botulinum* toxin belonging to *Clostridium botulinum* of types A, B, C, D, E, F, and G, or is a mixture of two or more of these types.

21. The process according to claim 20, wherein the *botulinum* toxin or the mixture of *botulinum* toxins is/are a *botulinum* neurotoxin or a composition of *botulinum* neurotoxins.

22. The process according to claim 18, wherein the fermentation step occurs in the first insulator and the purification (step) occurs totally or partially in a second insulator.

23. The process according to claim 18, wherein the fermentation step and a part of the purification occur in the first insulator and another part of the purification (step) occurs in the second insulator.

24. The process according to claim 18, wherein the fermentation step, a precipitation and filtration of a product of the fermentation step, occur in the first insulator as a part of the purification (step).

25. The process according to claim 18, wherein the first insulator and the second insulator are operated at the same temperature or at different temperatures.

26. The process according to claim 18, wherein the temperature in the first and/or the second insulator are changed according to each process step.

27. The process according to claim 26, wherein the temperature in the first insulator is in a range of approximately 20° to approximately 50° C. and the temperature in the second insulator is in a range of approximately -5° to approximately +25° C.

28. The process according to claim 18, wherein the process comprises the following steps:
a) in the first insulator
inoculating the fermentation media with a producing strain which produces a biologically active compound;
fermenting the producing strain;
separating the supernatant from the cells of the producing strain; and
precipitating the supernatant;
b) in the second insulator
centrifuging the precipitated supernatant to obtain a pellet;
extracting the pellet, centrifuging to obtain a supernatant;

precipitating the supernatant with subsequent centrifuging to obtain a supernatant;
c) in the first or the second insulator
precipitating the supernatant;
centrifuging the precipitate;
solubilizing the pellet obtained by centrifuging the precipitate;
dialysing the solubilized pellet and centrifuging the dialysate;
performing chromatography of the dialysate;
filtration of the dialysate to obtain an eluate.

\* \* \* \* \*